United States Patent [19]

Steiner et al.

[11] Patent Number: 4,477,451

[45] Date of Patent: Oct. 16, 1984

[54] 5,6-DIHYDRO-11-METHYLENEMORPHAN-THRIDIN-6-ONES, THEIR PREPARATION AND DRUGS CONTAINING THESE COMPOUNDS

[75] Inventors: Gerd Steiner, Kirchheim; Ludwig Friedrich, Bruehl; Dieter Lenke, Ludwigshafen, all of Fed. Rep. of Germany

[73] Assignee: BASF Aktiengesellschaft, Fed. Rep. of Germany

[21] Appl. No.: 482,004

[22] Filed: Apr. 5, 1983

[30] Foreign Application Priority Data

Apr. 6, 1982 [DE] Fed. Rep. of Germany ....... 3212794

[51] Int. Cl.³ .................... C07D 403/06; A61K 31/55
[52] U.S. Cl. ................ 424/248.54; 424/244; 260/239.3 T
[58] Field of Search ................ 260/239.3 T; 424/244, 424/248.54

[56] References Cited

U.S. PATENT DOCUMENTS 4,210,648  7/1980  Schmidt et al. ............ 260/239.3 T
4,213,985  7/1980  Schmidt et al. ............ 260/239.3 T
4,399,139  8/1983  Steiner et al. ............ 260/239.3 T

OTHER PUBLICATIONS

Arzneim.-Forsch. 27 (1977), 356.

*Primary Examiner*—Robert T. Bond
*Attorney, Agent, or Firm*—Keil & Weinkauf

[57] ABSTRACT

5,6-Dihydro-11-methylenemorphanthridin-6-ones of the formula I

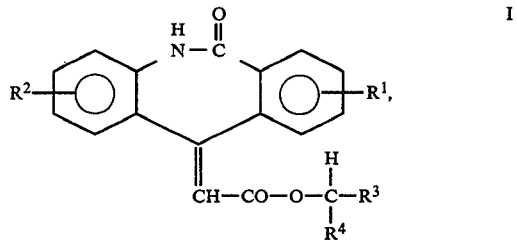

where $R^1$, $R^2$, $R^3$ and $R^4$ have the meanings given in the description, and their preparation and use.

The novel substances are particularly useful for treating gastric and duodenal ulcers.

18 Claims, No Drawings

5,6-DIHYDRO-11-METHYLENEMORPHANTHRI-DIN-6-ONES, THEIR PREPARATION AND DRUGS CONTAINING THESE COMPOUNDS

The present invention relates to 5,6-dihydro-11-methylenemorphanthridin-6-ones, processes for their preparation, therapeutic agents containing these compounds, and the use of these agents as drugs.

It has been disclosed that tricyclic ring systems of the 5,11-dihydro-6H-pyrido[2.3-b] [1.4]benzodiazepin-6-one type possess useful properties (Arzneim.Forsch. 27 (1977), 356; and German Laid-Open Applications DOS 2,724,501 and DOS 2,724,478), which enable them to be employed for the treatment of gastric and duodenal ulcers.

We have found that 5,6-dihydro-11-methylenemorphanthridin-6-ones of the formula I

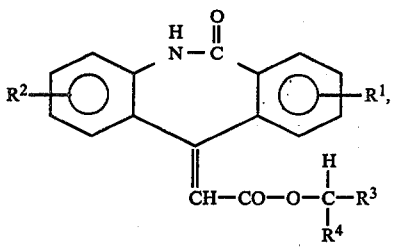

where $R^1$ and $R^2$ are each hydrogen, halogen, alkyl of 1 to 3 carbon atoms or trifluoromethyl, $R^3$ is aminoalkyl, where alkyl is of 1 to 3 carbon atoms, and the amine nitrogen atom can be substituted by 1 or 2 alkyl radicals of 1 to 3 carbon atoms or can form part of a 5-membered, 6-membered or 7-membered saturated ring which can contain a nitrogen, oxygen or sulfur atom as a further hetero atom or can contain a carbonyl group, and any nitrogen atom present can be substituted by alkyl of 1 to 3 carbon atoms or hydroxyalkyl of 2 or 3 carbon atoms or by phenyl which may be substituted by fluorine, chlorine, methoxy or methyl, and $R^4$ is hydrogen, or $R^3$ and $R^4$ together form a 5-membered, 6-membered or 7-membered saturated ring which can be substituted by one or more alkyl radicals of 1 to 3 carbon atoms, or can be converted to a bicyclic structure by an intramolecular methylene or bismethylene bridge and can contain a further nitrogen atom which can be substituted by alkyl of 1 to 3 carbon atoms or can be present in the form of the N-oxide, and their physiologically tolerated addition salts with acids, possess useful pharmacological properties.

The novel compounds of the formula I can occur as cis/trans isomers Ia and Ib:

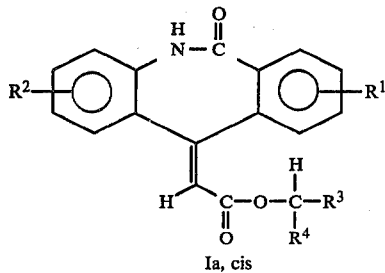

Ia, cis

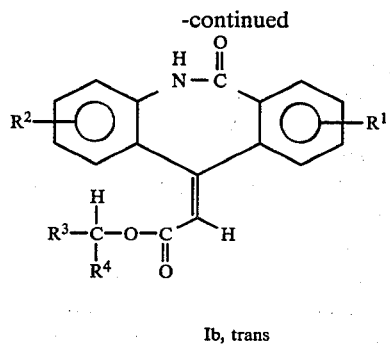

Ib, trans $R^1$ and $R^2$ are each preferably hydrogen, chlorine or methyl.

Specific examples of $R^3$ are aminomethyl, methylaminomethyl, dimethylaminomethyl, 2-dimethylaminoethyl, 4-methylpiperazin-1-ylmethyl, morpholin-1-ylmethyl, 3,5-dimethylmorpholin-1-ylmethyl, 2-morpholin-1-ylethyl, 1-methylmorpholin-3-yl, 1-benzylmorpholin-3-yl and 1-benzylmorpholin-6-on-3-yl, morpholin-1-ylmethyl being particularly preferred.

Cyclic structures $R^3$ and $R^4$ are, in particular, 1-methylpiperidin-4-yl and N-methyl-8-azabicyclo[3.2.1]octan-3-yl.

Compounds which are particularly active include cis,trans-11-(2-morpholin-1-yl)-ethoxycarbonylmethylene-5,6-dihydromorphanthridin-6-one, cis-11-(2-morpholin-1-yl)-ethoxycarbonylmethylene-5,6-dihydromorphanthridin-6-one, trans-11-(2-morpholin-1-yl)-ethoxycarbonylmethylene-5,6-dihydromorphanthridin-6-one, cis, trans-11-(2-dimethylamino)-ethoxycarbonylmethylene-5,6-dihydromorphanthridin-6-one and cis,-trans-11-(3-morpholin-1-yl)-propoxycarbonylmethylene-5,6-dihydromorphanthridin-6-one.

The novel compounds of the formula I are prepared by a process wherein
(a) a compound of the formula II

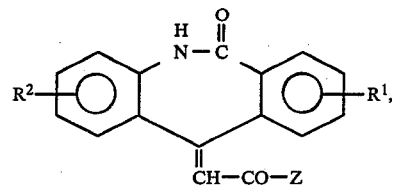

where $R^1$ and $R^2$ have the above meanings and Z is a nucleofugic leaving group, is reacted with an aminoalcohol of the formula III

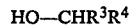

where $R^3$ and $R^4$ have the above meanings,
or, where $R^4$ is hydrogen,
(b) a compound of the formula IV

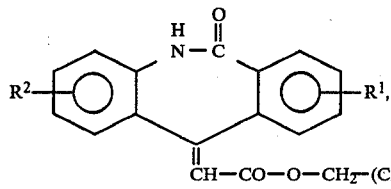

where Hal is halogen and n is 1, 2 or 3, is reacted with an appropriate amine, with nucleophilic substitution of the halogen, and, if required, the product thus obtained is separated into the pure cis and trans isomers and/or, if desired, converted to an addition salt with a physiologically tolerated acid.

A suitable nucleofugic leaving group Z is halogen, in particular chlorine.

Reaction (a) is advantageously carried out in the presence of one mole equivalent of a tertiary amine, eg. triethylamine, in an inert solvent, such as a cyclic saturated ether, in particular tetrahydrofuran or dioxane, or in a polar aprotic solvent, preferably dimethylformamide, at from 0° to 150° C., preferably at room temperature, and is in general complete in the course of from 3 to 10 hours.

If appropriate, the reaction can also be carried out in the presence of an excess of the aminoalcohol III employed, and this simultaneously serves as the solvent and, where relevant, as an acid acceptor.

Suitable nucleofugic groups are chlorine, bromine, iodine and alkylcarbonyloxy.

Reaction (b) is carried out in an excess of the appropriate amine, which simultaneously serves as the solvent, at from 50° to 150° C., preferably 110° C., or in an inert organic solvent.

The product is converted to the N-oxide in a conventional manner, advantageously with aqueous hydrogen peroxide in ethanolic solution. Conversion to an addition salt with a physiologically tolerated acid is likewise carried out in a conventional manner.

The compounds of the formula I are obtained as a rule in crystalline form, and can be purified by recrystallization from a conventional organic solvent, preferably a lower alcohol, eg. ethanol, or a lower ester, preferably ethyl acetate, or by column chromatography.

The resulting compounds according to the invention are, if desired, converted to addition salts with physiologically tolerated acids. Examples of suitable conventional physiologically tolerated organic or inorganic acids are hydrochloric acid, hydrobromic acid, phosphoric acid and sulfuric acid, and oxalic acid, maleic acid, fumaric acid, lactic acid, tartaric acid, malic acid, citric acid, salicylic acid, adipic acid and benzoic acid. Further acids can be found in, for example, J. Pharm. Sci. 66 (1977), 1.

The addition salts with acids are obtained as a rule in a conventional manner, by mixing the free base, or a solution thereof, with the appropriate acid, or a solution thereof, in an organic solvent, for example a lower alcohol, such as methanol, ethanol or propanol, a lower ketone, such as acetone, methyl ethyl ketone or methyl isobutyl ketone, or an ether, such as diethyl ether, tetrahydrofuran or dioxane. To achieve better precipitation of crystals, a mixture of any of the above solvents may also be used.

The starting compounds of the formula II are obtained by reacting a cis,trans-11-carboxymethylene-5,6-dihydromorphanthridin-6-one of the formula V

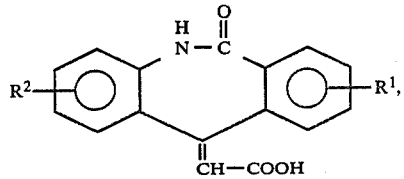

where $R^1$ and $R^2$ have the above meanings, with excess thionyl chloride in a conventional manner at room temperature to give the acyl chloride.

The compounds of the formula V are obtained by hydrolysis of the corresponding esters (German Laid-Open Application DOS 2,918,832) with alcoholic sodium hydroxide solution at from 40° to 90° C.

The compounds IV are obtained by reacting a compound II with a haloalcohol of the formula Hal—$(CH_2)_n$—OH, where Hal is halogen and n is 2, 3 or 4. The reaction can be carried out in an inert organic solvent or an excess of the haloalcohol at from 20° to 100° C.

To prepare the pure cis and trans isomers, the cis- and trans-carboxylic acid derivatives, respectively, of the formula V are preferably employed as starting materials. The isomer mixture is best separated by fractional crystallization, and the isomers are assigned on the basis of the NMR signals (270 MHz) of the 11-methylene proton at 6.12 and 6.18 ppm.

The individual isomers are assigned to the cis or trans series by, for example, X-ray structure analysis.

The novel compounds and their physiologically tolerated addition salts with acids are drugs which are useful for the treatment of disorders associated with pathologically increased gastric secretion, for example gastric and duodenal ulcers.

To investigate the antiulcerogenic action, 1 mg/kg of reserpine is administered intraperitoneally to groups of 10 female Sprague-Dawley rats each weighing 160–180 g, and the rats then remain without food for 18 hours (water ad libitum). This period is followed by intraperitoneal administration of 21.5 mg/kg of indometacin and oral administration of the test substance to the animals, which are then kept for 6 hours at 8° C., after which they are sacrificed. The stomachs are removed, and the area of ulcerous mucosal lesions is determined. The dose which reduces the ulcerous area by 50%, ie. the ED 50%, is determined from the linear regression between the logarithms of the doses administered and the relative reduction in the area of ulcerations, based on the control animals.

Pirenzepine (5,11-dihydro-11-[(4-methylpiperazin-1-yl)-acetyl]-6H-pyrido[2,3-b][1,4]benzodiazepin-6-one; German Pat. No. 1,795,183) is used as the reference substance.

The compounds according to the invention inhibit the formation of gastric ulcers, to an extent dependent on the dose (Table 1).

The actions of the compounds of Examples 3, 1, 2 and 15 are superior to the action of the known drug pirenzepine by a factor of from 3.4 to 10.2.

TABLE 1

| | Antiulcerogenic action on the rat | |
|---|---|---|
| Example No. | ED 50% mg/kg | Relative activity |
| 1, cis/trans | 1.90 | 3.4 |
| 1, cis | 1.50 | 4.3 |
| 1, trans | 5.30 | 1.2 |

TABLE 1-continued

| | Antiulcerogenic action on the rat | |
|---|---|---|
| Example No. | ED 50% mg/kg | Relative activity |
| 2 | 0.64 | 10.2 |
| 14 | 0.83 | 7.8 |
| pirenzipine | 6.5 | ≈1.0 |

The present invention therefore furthermore relates to drugs which contain a compound of the formula I or its physiologically tolerated addition salt with an acid, and to the use of the novel compounds in the treatment of disorders associated with pathologically increased gastric secretion.

The novel compounds may be employed in the conventional solid or liquid pharmaceutical forms, such as tablets, film tablets, powders, granules, coated tablets, suppositories or solutions. These are prepared in a conventional manner, and to do so the active compounds can be mixed with the conventional pharmaceutical auxiliaries, such as tablet binders, fillers, preservatives, tablet disintegrating agents, flow regulators, plasticizers, wetting agents, dispersants, emulsifiers, solvents, retarders and/or antioxidants (cf. H. Sucker et al.: Pharmazeutische Technologie, Thieme-Verlag, Stuttgart 1978). The formulations thus obtained normally contain from 0.1 to 99% by weight of the active compound.

The dosage of the compounds according to the invention depends on the age, condition and weight of the patient and on the route of administration. As a rule, the daily dose of active compound is from 5 to 100, preferably from 10 to 80, mg.

The Examples which follow illustrate the invention. The melting points of the cis/trans isomer mixtures can vary depending on the cis/trans ratio.

EXAMPLE 1 cis,trans-11-(2-Morpholin-1-yl)-ethoxycarbonylmethylene-5,6-dihydromorphanthridin-6-one a. Preparation of the starting material 200 ml of 10% strength sodium hydroxide solution were added to 30.0 g (108 millimoles) of 11-carbomethoxymethylene-5,6-dihydromorphanthridin-6-one in 150 ml of ethanol, the reaction mixture was stirred under reflux for 2 hours, then cooled and filtered, and the filtrate was evaporated down to about half its volume, under reduced pressure from a waterpump. The residue was acidified with concentrated hydrochloric acid, while cooling with ice, and the precipitated crystals were filtered off under suction and washed thoroughly with water. 27 g (94%) of cis,trans-11-carboxymethylene-5,6-dihydromorphanthridin-6-one of melting point 258°–260° C. were isolated.

200 ml of thionyl chloride were added to 31.0 g (124 millimoles) of the compound thus prepared, and the mixture was stirred at room temperature, a solution being obtained in the course of 1 hour. Stirring was continued for a further hour, after which the thionyl chloride was stripped off under reduced pressure from an oilpump, the residue was taken up with a little toluene and the solvent was once again stripped off completely. The cis,trans-11-chlorocarbonylmethylene-5,6-dihydromorphanthridin-6-dihydromorphanthridin-6-one which remained (yield 99%) was sufficiently pure for further reaction.

b. Preparation of the end product 19.6 g (150 millimoles) of N-(2-hydroxyethyl)morpholine and 12.5 g (124 millimoles) of triethylamine were added, a little at a time, to 35.1 g (124 millimoles) of 11-chlorocarbonylmethylene-5,6-dihydromorphanthridin-6-one (cis/trans isomer mixture) in 220 ml of dimethylformamide, while stirring thoroughly. The mixture was stirred under a nitrogen atmosphere for 2 hours at room temperature and then left to stand overnight, after which the solvent was completely distilled off under reduced pressure, the residue was partitioned between methylene chloride and water, the aqueous phase was rendered slightly alkaline with dilute sodium hydroxide solution and extracted twice with methylene chloride, and the combined organic phases were washed thoroughly with water, dried and evaporated down to give 46 g of crude product.

To prepare the pure cis/trans isomer mixture, the crude product was purified by column chromatography over silica gel, using a 95:5 mixture of methylene chloride and methanol. 31 g (66%) of colorless cis,trans-11-(2-morpholin-1-yl)-ethoxycarbonylmethylene-5,6-dihydromorphanthridin-6-one of melting point 92°–94° C. were isolated.

c. Separation of the isomer mixture

Separation of the mixture to give the cis and trans isomers is best carried out at the stage of 11-carboxymethylene-5,6-dihydromorphanthridin-6-one (cf. a):

20 g of cis,trans-11-(2-morpholin-1-yl)ethoxycarbonylmethylene-5,6-dihydromorphanthridin-6-one were dissolved in 1,200 ml of boiling methanol, the solution was filtered and the filtrate was subjected to fractional crystallization. 8.2 g of colorless crystals were isolated as the fraction of lowest solubility, and were shown by the 270 MHz NMR spectrum to be very rich in isomer A (methylene-H in the 11-position at 6.18 ppm in $D_6$-DMSO); this product was obtained in pure form (mp. 299°–301° C. (decomposition)) by a further recrystallization from methanol. X-ray structure analysis of isomer A established that the carboxylic acid group is trans to the carbonyl group of the acid amide structure in the 7-membered ring.

A mixed fraction followed by a 3rd or 4th fraction comprising 6.5 g of a product very rich in isomer B (methylene-H in the 11-position at 6.12 ppm in $D_6$-DMSO) crystallized out from the mother liquor.

Isomer B was purified by a further recrystallization from methanol; mp.: 297°–299° C. (decomposition).

From isomers A and B isolated in this manner, the pure cis and trans isomers of the end product were then obtained by procedures similar to those described in a and b. 5.0 g of isomer A gave, after the product had been purified by column chromatography (cf. b), 3,6 g (51%) of trans-11-(2-morpholin-1-yl)-ethoxycarbonylmethylene-5,6-dihydromorphanthridin-6-one of melting point 88°–90° C., while 3.6 g of isomer B gave 2.7 g (53%) of the corresponding cis-isomer of melting point 98°–100° C.

The following compounds were prepared by a procedure similar to that described in Example 1:
2.  cis,trans-11-(2-Dimethylamino)-ethoxycarbonylmethylene-5,6-dihydromorphanthridin-6-one. $H_2O$, mp. 78°–80° C.
3.  cis,trans-11-(3-Dimethylamino)-propoxycarbonylmethylene-5,6-dihydromorphanthridin-6-one.0.5 $H_2O$, mp. 74°–76° C.

4. cis,trans-11-[2-(4-Methylpiperazin-1-yl)]-ethoxycarbonylmethylene-5,6-dihydromorphanthridin-6-one.0.5 H₂O), mp. 87°–90° C.
5. cis,trans-11-(1-Methylmorpholin-3-yl)-methoxycarbonylmethylene-5,6-dihydromorphanthridin-6-one, mp. 103°–105° C.
6. cis,trans-11-(1-Benzylmorpholin-3-yl)-methoxycarbonylmethylene-5,6-dihydromorphanthridin-6-one.0.5 H₂O, mp. 81°–84° C.
7. cis,trans-11-(1-Benzylmorpholin-6-on-3-yl)-methoxycarbonylmethylene-5,6-dihydromorphanthridin-6-one.0.5 H₂O, mp. 91°–94° C.
8. cis,trans-11-(1-Methylpiperidin-4-yl)-oxycarbonylmethylene-5,6-dihydromorphanthridin-6-one, mp. 114°–116° C.
9. cis,trans-11-(N-Methyl-8-azabicyclo[3.2.1]octan-3-yloxycarbonylmethylene-5,6-dihydromorphanthridin-6-one.1.5 H₂O, mp. 133°–136° C. (column chromatography, 70:30 mixture of CH₂Cl₂ and methanol).
10. cis,trans-2-Chloro-11-(2-morpholin-1-yl)-ethoxycarbonylmethylene-5,6-dihydromorphanthridin-6-one, mp. 88°–90° C.
11. cis-trans-3-Methyl-11-(2-morpholin-1-yl)-ethoxycarbonylmethylene-5,6-dihydromorphanthridin-6-one, mp. 85°–87° C.

EXAMPLE 12 cis,trans-11-[2-(3,5-cis-dimethylmorpholin-1yl)]ethoxycarbonylmethylene-5,6-dihydromorphanthridin-6-one a. Preparation of the starting material cis,trans-11-(2-chloro)-ethoxycarbonylmethylene-5,6-dihydromorphanthridin-6-one 7.0 g (25 millimoles) of 11-chlorocarbonylmethylene-5,6-dihydromorphanthridin-6-one (cis/trans isomer mixture) were introduced, a little at a time, into 24 ml of 2-chloroethanol at room temperature, while stirring, and a slightly exothermic reaction took place. The reaction mixture was stirred for a further 3 hours, and was then poured onto ice water. The simi-crystalline precipitate was filtered off under suction and washed thoroughly with water. The crude product was then dissolved in 500 ml of methylene chloride, and the solution was washed with water and 0.5N sodium hydroxide solution. The organic phase was dried and evaporated down to give 7.6 g (92%) of a crude product in the form of an oil, which was sufficiently pure for the subsequent reaction.

b. Preparation of the end product 3.5 g (10.7 millimoles) of cis,trans-11-(2-chloro)-ethoxycarbonylmethylene-5,6-dihydromorphanthridin-6-one were stirred with 8 ml of cis-3,5-dimethylmorpholine for 3 hours at 110° C., and the mixture was cooled. The dark reaction mixture was then dissolved in about 200 ml of methylene chloride, and the solution was washed three times with water, the pH of the aqueous phase being brought to 8–9 during washing. The organic phase was dried and evaporated down to give a crude product in the form of a dark oil, which was purified by column chromatography on silica gel, using a 95:5 mixture of methylene chloride and methanol as the mobile phase. 2.4 g (55%) of colorless crystals of melting point 75°–78° C. were isolated.

The following compounds were obtained by a similar procedure:

13. cis,trans-11-[2-(3,5-trans-Dimethylmorpholin-1-yl)]ethoxycarbonylmethylene-5,6-dihydromorphanthridin-6-one, mp. 67°–69° C.
14. cis,trans-11-(3-Morpholin-1-yl)-propoxycarbonylmethylene-5,6-dihydromorphanthridin-6-one, mp. 79°–81° C.
15. cis,trans-11-(2-Methylmorpholin-1-yl)-ethoxycarbonylmethylene-5,6-dihydromorphanthridin-6-one, mp. 76°–78° C.
16. cis,trans-11-(Thiamorpholin-1-yl)-ethoxycarbonylmethylene-5,6-dihydromorphanthridin-6-one, mp. 83°–85° C.

We claim:

1. A 5,6-dihydro-11-methylenemorphanthridin-6-one compound of the formula I

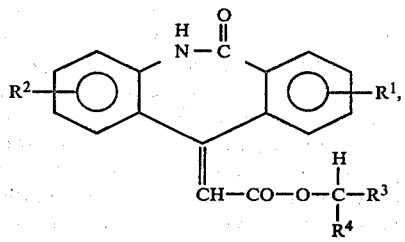

where $R^1$ and $R^2$ are each hydrogen, halogen, alkyl of 1 to 3 carbon atoms or trifluoromethyl, $R^3$ is aminoalkyl, where alkyl is of 1 to 3 carbon atoms, and the amine nitrogen atom can be substituted by 1 or 2 alkyl radicals of 1 to 3 carbon atoms and can form part of a morpholine ring and $R^4$ is hydrogen, or $R^3$ and $R^4$ together with the carbon to which they are attached form a 6-membered saturated ring which can be converted to a bicyclic structure by an intramolecular methylene or bismethylene bridge and can contain a further nitrogen atom which can be substituted by alkyl of 1 to 3 carbon atoms, and its physiologically tolerated addition salts with acids.

2. A compound of the formula I as described in claim 1, where $R^1$ and $R^2$ are each hydrogen, chlorine or methyl, $R^3$ is aminoalkyl, where alkyl is of 1 to 3 carbon atoms and the amine nitrogen atom can be substituted by 1 or 2 alkyl radicals of 1 to 3 carbon atoms or can form part of a morpholine ring, and $R^4$ is hydrogen, or $R^3$ and $R^4$ together with the carbon to which they are attached form a 6-membered saturated ring which can be converted to a bicyclic structure by an intramolecular methylene or bismethylene bridge and may contain a further nitrogen atom which can be substituted by alkyl of 1 to 3 carbon atoms, and its physiologically tolerated addition salts with acids.

3. A compound of the formula I as described in claim 1, where $R^1$ and $R^2$ are each hydrogen, chlorine or methyl, $R^3$ is morpholin-1-ylmethyl or 2-morpholin-1-ylethyl, where the morpholine ring can be monosubstituted or disubstituted by methyl, or $R^3$ is aminomethyl which can be substituted at the amino group by 1 or 2 methyl groups, and $R^4$ is hydrogen, or $R^3$ and $R^4$ together with the adjacent C-atom form a N-methyl-8-azabicyclo octane residue and its physiologically tolerated addition salts with acids.

4. A compound of the formula I as described in claim 1, in the cis-form.

5. A compound of the formula I as described in claim 2, in the cis-form.

6. A compound of the formula I as described in claim 3, in the cis-form.

7. A compound of the formula I as described in claim 1, in the trans-form.

8. A compound of the formula I as described in claim 2, in the trans-form.

9. A compound of the formula I as described in claim 3, in the trans-form.

10. cis,trans-11-(2-Morpholin-1-yl)-ethoxycarbonylmethylene-5,6-dihydromorphanthridin-6-one.

11. cis-11-(2-Morpholin-1-yl)-ethoxycarbonylmethylene-5,6-dihydromorphanthridin-6-one.

12. trans-11-(2-Morpholin-1-yl)-ethoxycarbonylmethylene-5,6-dihydromorphanthridin-6-one.

13. cis,trans-11-(2-Dimethylamino)-ethoxycarbonylmethylene-5,6-dihydromorphanthridin-6-one.

14. cis,trans-11-(3-morpholin-1-yl)-propoxycarbonylmethylene-5,6-dihydromorphanthridin-6-one.

15. A therapeutic agent for treating disorders associated with pathologically increased gastric secretion comprising a pharmaceutical carrier and an effective amount of a compound as defined in claim 1 as the active ingredient.

16. A method of treating a disorder associated with pathologically increased gastric secretion, in a patient suffering therefrom, which comprises administering an effective amount of a compound as defined in claim 1.

17. cis,trans-11-(3-Dimethylamino)-propoxycarbonylmethylene-5,6-dihydromorphanthridin-6-one.

18. cis,trans-11-(N-Methyl-8-azabicyclo [3.2.1]octane-3-yloxycarbonylmethylene-5,6-dihydromorphanthridin-6-one.

* * * * *